United States Patent [19]

Huang

[11] 4,279,994
[45] Jul. 21, 1981

[54] LIPASE DETERMINATION METHOD AND REAGENT

[75] Inventor: Cleo L. Huang, Carmel, Ind.

[73] Assignee: The Dow Chemical Company, Midland, Mich.

[21] Appl. No.: 57,525

[22] Filed: Jul. 13, 1979

[51] Int. Cl.$^3$ .............................................. C12Q 1/44
[52] U.S. Cl. .................................... 435/19; 435/184; 435/810; 23/230 B
[58] Field of Search ................... 435/18, 19, 184, 805, 435/808, 810; 23/230 B; 252/408 R

[56] References Cited

U.S. PATENT DOCUMENTS

| | | | |
|---|---|---|---|
| 3,119,668 | 1/1964 | Ellman | 23/230 |
| 3,867,259 | 2/1975 | Forgione | 435/805 |
| 3,875,014 | 4/1975 | Forgione | 435/805 |
| 3,917,515 | 11/1975 | Goldberg | 435/19 |
| 3,986,930 | 10/1976 | Kurooka et al. | 435/19 |

FOREIGN PATENT DOCUMENTS 52-151091 12/1977 Japan .

OTHER PUBLICATIONS

Chemical Abstracts, vol. 70, 113805e, 1969.
Kurooka et al., J. Biochem., 81, 361-369 (1977).
Gomori, J. Clin. Pathol. 27, 170-182, (1957).
Clinical Chemistry: Principles and Technics, Second Edition Ed Henry, Cannon & Winkelman, Harper & Row, Md. (1974), pp. 917-919.
Chemical Abstracts, vol. 81, 21034b (1974).

Primary Examiner—Ernest G. Therkorn

[57] ABSTRACT

An improved reagent and method for determination of lipase in biological fluids utilizes an S-acyl compound as the substrate and a chromogenic sulfhydryl reagent to develop a measureable color. The improved reagent and method include a solid, water soluble pseudocholinesterase inhibitor, preferably eserine salicylate. Albumin may also included to increase sensitivity. Lipase is measured by incubating a specimen with the S-acyl compound, chromogenic sulfhydryl reagent and pseudocholinesterase inhibitor; terminating the incubation by adding a non-ionic surfactant; measuring the resulting color directly, and comparing the color to that obtained with a chemical standard solution containing an S-(2-aminoalkyl) isothiouronium salt.

5 Claims, No Drawings

LIPASE DETERMINATION METHOD AND REAGENT

BACKGROUND OF THE INVENTION

This invention concerns an improvement in the lipase determining method and reagent of Kurooka et al., U.S. Pat. No. 3,986,930, and Kurooka et al., J. Biochem. 81,361–369 (1977) and Kurooka, Japanese Patent Application No. Sho. 51-68342, the disclosures of which are hereby incorporated by reference. In this method and reagent, an S-acyl compound is provided as a substrate. Suitable S-acyl compounds are described in the above references. Lipase in a biological fluid specimen such as serum or plasma catalyzes the hydrolysis of the S-acyl compound, releasing sulfhydryl groups. The release sulfhydryl groups are reacted with a chromogenic sulfhydryl reagent, such as 5,5'-dithiobis(2-nitrobenzoic acid) ["DTNB" as abbreviated by Kurooka et al.] and the resulting color is measured to provide a measurement of lipase activity. Suitable chromogenic sulfhydryl reagents are disclosed by Kurooka et al. and by Ellman, U.S. Pat. No. 3,119,668, the disclosure of which is hereby incorporated by reference.

The above method and reagent has many desirable features. However, as disclosed in the Kurooka Japanese patent application, it suffers from a lack of sensitivity, which Kurooka attributed to inhibition by serum albumin. It also lacks specificity for lipase, and does not always measure true lipase activity. Additionally, the method requires addition of acetone to precipitate protein prior to measurement, requiring centrifugation or a similar protein removal step prior to measurement.

Eserine, also named as physostigmine, is a plant alkaloid extracted from calabar beans.

BRIEF SUMMARY OF THE INVENTION

It has now been discovered that the specificity of the Kurooka et al. method and reagent can be greatly improved by the addition of a pseudocholinesterase inhibitor, so that the resulting reagent and method are more truly specific for lipase. It has been further discovered that sensitivity of the method can be improved by inclusion of a minor amount of albumin. The test procedure can also be improved by utilizing an anionic surfactant to terminate the incubation, and that the color can then be measured directly, without centrifugation or other protein removal operations. It has been further discovered that water soluble S-(aminoalkyl) isothiourium salts can be employed as standard solutions in the Kurooka et al. method and reagent. The invention thus includes a novel improved reagent, method and diagnostic test kit.

The reagent, method and kit of the invention all include an S-acyl compound and a chromogenic sulfhydryl reagent, and can also include a carboxylesterase and arylesterase inhibitor as disclosed by Kurooka and Kurooka et al. The same S-acyl compounds and chromogenic sulfhydryl reagents can be used, and these terms are employed herein with the same meanings as in Kurooka et al. U.S. Pat. No. 3,986,930 hereby incorporated by reference. The presently preferred s-acyl compound is 2,3-dimercaptopropan-1-ol tributyrate, abbreviated as "BALB", by Kurooka et al., and also preferred by them. The peferred chromogenic sulfhydryl reagent is "DTNB", 5,5'-dithiobis(2-nitrobenzoic acid), also preferred by Kurooka et al. The preferred inhibitor of arylesterase and carboxylesterase is phenyl methyl sulfonyl fluoride (abbreviated "PMSF"), also preferred by Kurooka et al.

It has been found that the S-acyl compounds are quite susceptible to hydrolysis by pseudocholinesterase found in biological fluids such as human blood serum. As a result, the color produced on reaction with the chromogenic sulfhydryl reagent can be elevated so that falsely elevated lipase results are obtained.

The solid, water soluble pseudocholinesterase inhibitor can be any pseudocholinesterase inhibitor which is diagnostically-acceptable; that is, physically and chemically stable and soluble in the aqueous incubation mixture, and capable of inhibiting pseudocholinesterases present in biological fluids without inhibiting lipase or interfering with the color reaction with the sulfhydryl reagent. Pseudocholinesterase inhibitors and cholinesterase inhibitors are toxic and must be handled with appropriate precautions. The use of volatile cholinesterase inhibitors can lead to production of toxic vapors during the test incubation as well as to loss of the inhibitor from the substrate during incubation or preparative preheating. In the preparation of lyophilized regents for diagostic kits, the inhibitor must be non-volatile under the conditions used to remove water from the other reagents (temperatures on the order of $-50°$ C. to $+35°$ C. at pressures of 0.1 to 5 millimeters of mercury, for 12 to 48 hours). They must also be physically and chemically compatible with the other ingredients, and readily water dispersible from the dry form, as well as water soluble. Whether or not a particular cholinesterase inhibitor has the requisite properties of inhibiting activity, inertness to lipase, non-volatility, lyophilizability, and water dispersibility and solubility, can be ascertained in many cases from its known properties, or by routine testing.

In general, the pseudocholinesterase inhibitor should be a solid at temperatures below about 50° C., should have good water solubility (at least 0.5 to 25 millimoles per liter), should have a vapor pressure substantially below that of water, and should be chemically stable in aqueous solutions at neutral to basic pHs. A number of the liquid phosphate insecticide cholinesterase inhibitors are thus not suitable. Parathion, for example, is not only a highly toxic liquid, but also has insufficient water solubility and insufficient stability at alkaline pH. Isofluorphate, or diisopropyl fluorophosphate, decomposes in the presence of moisture, forming hydrogen fluoride and losing inhibitory activity, as well as being volatile, highly toxic, and unlyophilizable. Malathion is a liquid with insufficient water solubility and is subject to hydrolysis and loss of activity at alkaline pH.

Pseudocholinesterase inhibitors which are suitable in the invention include the solid, water soluble, carbamate cholinesterase/pseudocholinesterase inhibitors such as physostigmine (eserine), neostigmine, pyridostigmine bromide, ambenonium chloride, benzpyrinium chloride, demecorium bromide. Eserine (physostigmine) and its salts such as the salicylate and sulfate are preferred for use as pseudocholinesterase/cholinesterase inhibitors. Eserine salicylate is highly specific for serum pseudocholinesterase, and does not inhibit lipase under the test conditions. Also, it does no interfere with the sulfhydryl color reaction under the conditions of use. Eserine salicylate is preferred. The inhibitor is employed in an amount sufficient to inhibit pseudocholinesterase and cholinesterase in the specimen. The optimum amounts to be employed in specific formulations and procedures can be determined by conventional range finding experiments. With the preferred eserine salicylate, a concentration of at least about 0.005 millimolar (0.005 thousandths of a gram molecular weight per liter) in the mixture of substrate reagent and specimen is useful, and concentrations of from about 0.01 to about 0.03 are preferred. Higher concentrations can be employed (from 0.005 to 0.1 millimolar to saturation), however, little or no improvement has been observed with concentrations increasing from 0.02 to 0.05 millimolar, and additional amounts are generally not needed. With concentrations substantially below about 0.005 millimolar, serum pseudocholinesterase can release sulfhydryl groups from the S-acyl compound, giving falsely elevated lipase measurements.

Albumin is employed in a sensitivity enhancing amount. The exact amount to be employed in particular cases can be determined by conventional range finding techniques using different concentrations of albumin. Insufficient albumin, as well as excess albumin, results in a loss in sensitivity as indicated by a loss in color developed for a given amount of lipase. Generally an albumin concentration of from about 1 to about 8 milligrams per milliliter of reagent gives good results. An anionic surfactant such as sodium dodecyl sulfate is preferably included to enhance enzyme activation, as described by Kurooka et al., J. Biochem. 81, 361–69 (1977).

According to the invention, a biological fluid sample such as serum, plasma, pancreatic fluid or the like, is incubated with the reagent containing the S-acyl compound, chromogenic sulfhydryl reagent, eserine salt and albumin under conditions of pH and temperature conducive to lipase activity. After a predetermined incubation period, the incubation is terminated, the turbid mixture is clarified and the resulting color is measured in a colorimeter or spectrophotometer. It has been found that the incubation can be terminated and the mixture clarified simultaneously by the addition of a substrate solubilizing, non-ionic surfactant, such as an alkyl phenyl ether of polyethylene glycol, polyoxyethylene sorbitan mono fatty acid esters or polyethoxylated vegetable oil.

The term "substrate solubilizing" is employed to refer to the property of the non-ionic surfactant to solubilize the S-acyl compound in water, forming a clear solution of the S-acyl compound in the reagent mixture, rather than an emulsion. As described by Kurooka et al., the S-acyl substrate compound forms a micellar emulsion in aqueous buffer without a surfactant or emulsifier. Particular non-ionic surfactants can be tested for substrate solubilizing ability simply by adding them to the aqueous buffered S-acyl substrate emulsion, at a pH of about 8 to 9 and observing to ascertain whether the non-aqueous phase becomes miscible in the aqueous phase. Suitable non-ionic, substrate-solubilizing surfactants include octyl phenoxy polyethoxy ethanol (Triton X-100, Rohm & Haas, average molecular weight 646, Merck Index, Ninth Ed., Monograph 7350); nonyl phenol polyethylene glycol ether (Tergitol NPX, Union Carbide); polyoxyethylated vegetable oil (Emulphor EL-719, GAF Corporation); polyoxyethylene (20) sorbitan monopalmitate (Tween 40, ICI United State) and Cremophor, E-L, BASF-Wyandotte. Anionic surfactants such as sodium lauryl sulfate and some non-ionic surfactants such as polyoxyethylene (23) lauryl ether leave the S-acyl compound substrate in emulsion form.

The non-ionic substrate solubilizing surfactant disrupts and dissolves the substrate micelles, simultaneously terminating lipase activity and clarifying the mixture so that the color can be measured directly, without an intermediate precipitation, centrifugation, or other separation step. While the non-ionic surfactant alone is sufficient to terminate the incubation and allow direct measurements, it is preferred also to add sufficient acid to reduce the pH to about 7.0 or below. The combined use of acidification and the non-ionic surfactant provides a more stable final color in the mixture. In a preferred procedure, a solution of about 0.5–2.0 grams of an octylphenoxy polyethoxyethanol (Triton X-100, Rohm & Haas) in 100 milliliters of an acidic solution such as 16.5 millimolar aqueous hydrochloric acid* is used to terminate the incubation, using two milliliters of this acid reagent to about one milliliter of reaction mixture.

* or Tris-HCl (1.5–2.5 Molar)

DETAILED DESCRIPTION

The reagent substrate composition of the invention typically comprises the following ingredients in the following amounts.

| | |
|---|---|
| Buffer for pH 8.0–9.5 | 0.05–0.3 Molar |
| Anionic surfactant | 1–3 Millimolar (mM) |
| Chromogenic Sulfhydryl Reagent | 0.15–0.8 mM |
| Carboxylesterase Inhibitor | 0.05–1.5 mM |
| Eserine salt | 0.005–0.1 mM |
| Albumin | 1–8 mg/ml |
| S-Acyl compound | 2–5 mM |

In the method of the invention, an aqueous mixture of the above ingredients is mixed with the specimen, in a ratio of about 2 milliliters of the reagent substrate to from about 10 to about 100 microliters of specimen, and the mixture is incubated at about 20° to 25° to about 37° C. for from about 15 to 45 minutes. The acid reagent and non-ionic surfactant are then added and the color is measured, preferably by measuring absorbance in a spectrophotometer with light having a wavelength of 400 to 420 nanometers ("nm"). The lipase activity can be determined by comparison to results obtained with standard solutions of known lipase activity, calibration charts or the like. Preferably a blank measurement is also obtained, by using duplicate specimens; and terminating the incubation early with one of the duplicates to obtain a blank value.

It is also desirable to utilize a standard solution which will give a predetermined color or absorbance which is correlated to a known amount of lipase activity. Standard lipase solutions or control sera can be used; however, these are subject to variations from one batch to the next, and loss of lipase activity in storage. A non-enzymatic chemical standard normally permits the standard solution to be formulated to give uniform calibration from batch to batch, and improve storage characteristics necessary for use with premixed reagents and diagnostic kits. Although many compounds will react with the chromogenic sulfhydryl reagent, they are not useable as standards. For example, S-acetylthiocholine bromide and 2-methyl-3-acetyl mercaptopropionic acid react so slowly with the sulfhydryl reagent that the color reaction is incomplete after the incubation. Mercaptopurine and thiolactic acid provide an unstable color. Other compounds, such as dithiothreitol and 2-mercaptothiazoline are either unstable, or are insoluble in the incubation mixture.

It has now been found that the diagnostically acceptable water soluble S-(2-aminoloweralkyl) isothiuronium salts can be used as chemical standards in the lipase determination method. Such salts, wherein "loweralkyl" is 1, 2 or 3 carbon atoms, and where the anionic moiety does not inhibit, participate in or otherwise interfere with the color reaction, have the necessary stability, reactivity with the chromogenic sulfhydryl reagent, and solubility to provide excellent results as chemical standards. The preferred compound is S-(2-aminoethyl) isothiuronium bromide hydrobromide. The standard solution comprises the isothiuronium salt in water, in a predetermined concentration adapted to provide a color on reaction with the lipase reagents, which color corresponds to a predetermined known level of lipase activity. Typically the isothiuronium salt should be employed in an amount which will give an absorbance of from about 0.1 to about 0.5 to about 1 in the final reaction mixture, after incubation and reaction with the chromogenic sulfhydryl reagent. Preferably, the isothiuronium salt is admixed with a buffer or acid to provide a pH in aqueous solution of from about 6.2 to 7.0. For premixed reagents or diagnostic kits, the isothiuronium salt and buffer can be formulated and dried, by lyophilization for example, to be reconstituted with distilled water before use. Also, the isothiuronium salt can be lyophilized with a stabilizer such as dextran, and reconstituted with aqueous acid, such as 0.2 Normal hydrochloric acid. A suitable lipase color standard composition can be prepared as follows:

For a standard color composition corresponding to high normal human serum lipase levels (about 200 International Units per milliliter):

S-(2-aminoloweralkyl)isothiuronium salt
1.1 milligrams buffer (pH 6.5)
Water q.s. to one milliliter 20 Microliters of this solution is a typical amount used per test, with about 1.1 milliliters of the substrate-reagent composition, to give a final absorbance of about 0.4. The exact absorbance and correlation to a particular lipase level will depend on the exact proportions of isothiuronium salt used in the final mixture.

A preferred reagent substrate comprises the following:

| Buffer-Tris Buffer | 0.12 Molar |
|---|---|
| Sodium Dodecyl Sulfate | 2 mM (millimolar) |
| DTNB | 0.3 mM |
| PMSF | 0.4 mM |
| Eserine Salicylate | 0.03 mM |
| Albumin | 7.0 mg/ml |
| BALB | 3.0 mM |
| Final pH | 8.8 |

In a preferred procedure, 1.1 to 2.1 milliliters of the above reagent are used with a 20–50 microliter sample. Incubation is preferably at 30° C. for 20 to 30 minutes, after which the reaction is stopped by addition of 2 milliliters of 0.6 to 0.8 percent (weight by volume) Triton X-100 in 16.5 mM hydrochloric acid.* Absorbance is measured at 412 nanometers, and compared to the results obtained with a duplicate specimen when absorbance is measured after 10 minutes incubation. The difference in absorbance is used as a measurement of lipase activity.

*or an acid solution (pH 1-5) such as Tris-HCl (1.5-2.5 Molar, pH about 4.0).

In a form particularly preferred for kit applications, the reagent substrate, an acid-non-ionic surfactant reagent and chemical color standard are prepared as five separate compositions:

(a) Buffer (pH 9.2–9.5), albumin, eserine salt, anionic surfactant and carboxylesterase inhibitor, optionally with a lyophilization stabilizer such a dextran, e.g., Dextran 2000, in lyophilized form.

(b) Buffer (pH selected to stabilize the chromogenic sulfhydryl reagent, preferably pH 6.8 to 7.2), chromogenic sulfhydryl reagent and dextran lyophilization stabilizer in lyophilized form.

(c) S-Acyl Compound solution in a water-miscible inert solvent, preferably about 33 millimolar in ethanol.

(d) Non-ionic surfactant (Triton X-100, about 0.75%) in about 2.0 m Tris-HCL (Tromethamine HCL), as the stopping reagent.

(e) S-(aminoloweralkyl)isothiouronium halide hydrohalide salt (about 1.1 milligrams) in lyophilized form in a container adapted for reconstitution with 0.2 Normal aqueous hydrochloric acid to one milliliter.

The relative concentrations and pH's used in compositons (a) and (b) are selected so that after reconstitution with distilled water and mixing to give the required final concentration, the combination of buffers in components (a), (b) and (c) provide a final pH conducive to lipase activity, preferably a pH of about 8.5–9.5. The reconstituded sulfhydryl reagent is more stable when prepared separately at a pH near neutrality. The acidic, non-ionic surfactant solution is adapted, when combined with the other components, to inactivate the lipase by low pH and micelle disruption and to clarify the mixture without precipitation, so that color can be measured directly.

The invention is further illustrated by the following examples.

EXAMPLE 1

(a) A Lyophilized Substrate Reagent is prepared to contain:

| Tris Buffer (pH 9.2–9.4) | 0.11 grams |
|---|---|
| Albumin | 77 milligrams (mg) |
| Eserine Salicylate | 0.18 mg |
| Dextran 2000 | 5 mg |
| Sodium Dodecyl Sulfate | 6.335 mg |
| Phenylmethylsulfonyl-fluoride ("PMSF") | 0.765 mg |
| Distilled water | q.s. to 3 ml |
| mixed and lyophilized. | |

(c) Lyophilized DTNB is prepared to contain:

| Tris Buffer (pH 6.85) | 0.188 grams |
|---|---|
| DTNB | 14.25 mg |
| Dextran 200 | 5 mg |
| Distilled water mixed and lyophilized. | q.s. to 3 ml |

(c) BALB Substrate is prepared by dissolving BALB in ethanol to a BALB concentration of 33 millimolar.

(d) Stopping Solution is prepared by dissolving 0.6 grams of non-ionic surfactant (Triton X-100) in 16.5 millimolar hydrochloric acid.

The above four compositions comprise a diagnostic kit.

EXAMPLE 2

The four-reagent kit of Example 1 is utilized as follows, using duplicate specimen vials labelled "Patient- Blank", "Patient", "Blank 10 Minutes" and "Blank 30 Minutes", and the following procedure.

(a) Transfer 10.0 ml distilled water into Lyophilized Substrate Reagent vial and dissolve by inversion.

(b) Transfer 1.0 ml of the BALB Lipase Substrate into above vial and mix well by inversion.

(c) Transfer 12 ml of distilled water into Lyophilized DTNB reagent vial. Dissolve by inversion.

(d) Pipet 0.1 ml of above DTNB solution into the marked vials.

(e) Pipet 1.0 ml of the mixture of BALB Substrate and Substrate Reagent into each marked vial and mix with gentle swirling. The resulting mixture is a substrate containing an emulsion of the BALB in a solution of the other reagents.

(f) Incubate all vials, now containing the complete substrate reagent composition in a 30° C. heat source for 10 minutes.

(g) At timed intervals, add 0.05 ml of serum to duplicate patient-blank vial and patient vials and add 0.05 ml distilled water to a "Blank 10 Minute" vial, appropriately labelled.

(h) After 10 minutes (with same sequence and intervals as instituted in Step (g), add 2.0 ml of Stopping Reagent to the "Patient Blank" and "Blank 10 Minute" vials.

(i) After 30 minutes, add 2.0 ml of Stopping Reagent to the "Patient" vial and "Blank-30 minutes" vial.

(j) Set spectrophotometer at 412 nanometers and zero the instrument with a vial of distilled water.

(k) Record the absorbance of vials in each ccase 5 minutes after addition of the Stopping Solution.

The activity of serum lipase is proportional to the absorbance at 412 nanometers, and is calculated as follows:

Lipase activity per 20 minutes = Absorbance [patient vial-Blank vial] (30 minutes) -Absorbance [patient vial-Blank vial] (10 minutes)

EXAMPLE 3

Precision of the method of the above examples was tested using seven runs on "abnormal" elevated lipase control serum and a "normal" control serum and using an incubation period of 35 minutes so the difference in absorbance was measured over a 25 minute period (Absorbance/25). In both cases excellent precision was obtained, with standard deviations of ±0.028 and ±0.029.

Analysis of serum samples from 15 apparently normal humans gave normal results (Absorbance/25=0.2) in 93 percent of the cases compared to 93 percent normal identification with a commercial reference method (DuPont ACA turbidometric procedure). The highest apparent normal result gave an absorbance/25 of 0.252.

Sixteen serum samples from diagnosed pancreatitis patients gave results greater than 0.3 in all cases. In some cases of high lipase activity the serum specimen was diluted 1:10 before analysis, and the results multiplied by 10.

Fifteen serum specimens from patients with high esterase levels, including nine with elevated cholinesterase were analyzed. Three of these gave abnormal results (absorbance/25=above 0.3), and two of these three were confirmed as elevated by a turbidometric reference lipase method and by elevated or borderline amylase results. One additional specimen had a high borderline lipase result between 0.2 and 0.3 (Absorbance/25).

The above results indicate that the invention measures lipase activity and gives results whch distinguish normal from abnormal levels even in the presence of cholinesterase, with a reliability at least as great as prior turbidometric methods.

EXAMPLE 4

A reagent composition is formulated to contain the following:

| | |
|---|---|
| Tris Buffer | 0.12 Molar |
| Sodium Dodecyl Sulfate | 2 Millimolar ("mM") |
| DTNB | .3 mM |
| PMSF | 0.4 mM |
| BALB | 3 mM |

Final pH about 8.8. Using a procedure similar to that of Example 2, the reagent was used to assay solutions containing 1.17 units of acetyl cholinesterase (a true cholinesterase) or 0.36 units of butyryl cholinesterase (a pseudocholinesterase). Acetyl cholinesterase produced an absorbance change of 0.011 absorbance units and butyryl cholinesterase produced a change of 0.421 absorbance units. These results, obtained with no lipase and no eserine salt; indicate that the true cholinesterases, has some effect and that the pseudocholinesterases which are found in serum, can give falsely elevated lipase results.

Using fresh human serum specimens, different amounts of eserine salicylate were added and the absorbance change between 10 and 30 minutes incubation was noted. Eserine salicylate was added as a 1 millimolar solution.

| Eserine salicylate added | Absorbance change |
|---|---|
| 0 | 0.604 |
| 5 microliters (0.005 millimolar) | 0.501 |
| 10 microliters | 0.495 |
| 20 microliters | 0.475 |
| 30 microliters | 0.490 |
| 40 microliters | 0.496 |
| 50 microliters | 0.492 |

The above results indicated inhibition of pseudocholinesterase by eserine salicylate, with more specific measurement of lipase activity.

EXAMPLE 5

In a procedure similar to that of Example 4, neostigmine methylsulfate, eserine salicylate and PMSF were compared to inhibit acetyl cholinesterase (10.4 units per ml); the pseudocholinesterase butyryl cholinesterase (7.2 units per ml) or human serum containing naturally occurring pseudocholinesterases. Fifty microliters of serum or of the cholinesterase or pseudocholinesterase wre used, and the absorbance change over a 20 minute incubation was recorded. The following results were obtained.

TABLE II

| | Acetyl Cholinesterase | Butyryl Cholinesterase | Serum A | Serum B |
|---|---|---|---|---|
| No Inhibitors | 0.013 | 0.343 | 0.482 | 0.379 |
| Eserine Salicylate* | 0.027 | 0.182 | 0.078 | 0.092 |
| Neostigmine Methyl Sulfate* | 0.025 | 0.187 | 0.098 | 0.081 |
| PMSF*** | 0.021 | 0.338 | 0.487 | 0.383 |
| Eserine* + PMSF*** | 0.013 | 0.179 | 0.087 | 0.077 |

TABLE II-continued

| | Acetyl Cholinesterase | Butyryl Cholinesterase | Serum A | Serum B |
|---|---|---|---|---|
| Neostigmine** + PMSF*** | 0.018 | 0.169 | 0.063 | 0.068 |

*Eserine Salicylate - 0.037 μm (micromolar)
**Neostigmine Methyl Sulfate - 0.037 mM (millimolar)
***PMSF - 0.37 mM
Activity is expressed as ΔAbsorbance per 20 minutes incubation.

The results in Table II show a significant increase in absorbance with the pseudocholinesterase, butyryl cholinesterase, as compared with the cholinesterase, acetyl cholinesterase, indicating significant hydrolysis of the BALB substrate by pseudocholinesterase. The data also show significant inhibition by eserine salicylate and neostigmine, alone or in combination with PMSF. In the serum samples, the data indicate that the carboxylesterase-arylesterase inhibitor PMSF has little or no effect in inhibiting the interfering hydrolysis of the S-acyl compound, except when the pseudocholinesterase inhibitor is present.

EXAMPLE 6

The compositions of Example 1 are prepared and packaged as a diagnostic kit which also includes, as a standard, 5.5 milligrams of S-(2-aminoethyl)-isothiuronium bromide hydrobromide in a container adapted for dilution to 5.0 milliliters with 0.2 normal hydrochloric acid.

EXAMPLE 7

The compositions of Example 1 are prepared except that albumin is omitted from composition (a) and composition (b) is prepared as follows:

| | |
|---|---|
| Tris Buffer (pH 6.85) | 0.0605 grams |
| DTNB | 7.18 mg |
| Albumin | 0.423 grams |
| Distilled water mixed and lyophilized. | q.s. to 4 ml |

The compositions are used as in Example 2 except that in step (c) the DTNB reagent is reconstituted with 5.5 ml of water and in step (d), 1.1 ml of this solution is used.

Twenty microliters of the standard solution of Example 6 is used as a standard in additional vial labeled "Standard."

I claim:
1. In a method of determining lipase activity in biological fluids by incubating a biological fluid specimen in the presence of an S-acyl compound, a chromogenic sulfhydryl reagent and a carboxyesterase inhibitor and measuring the resulting color, the improvement which comprises:
   (a) carying out said incubation in the presence of a diagnostically-acceptable cholinesterase/-pseudocholinesterase inhibitor in a concentration sufficient to inhibit cholinesterase and pseudocholinesterase in the specimen;
   (b) incubating a diagnostically-acceptable S-(aminoloweralkyl)isothiuronium salt with said S-acyl compound, chromogenic sulfhydryl reagent and said inhibitors;
   (c) measuring the color obtained; and
   (d) comparing the color measurements.
2. The method of claim 1 wherein said isothiuronium salt comprises S-(2-aminoethyl)-isothiuronium bromide hydrobromide.
3. The method of claim 1 wherein the cholinesterase/pseudocholinesterase inhibitor is an eserine salt.
4. In a method for determination of lipase activity in biological fluids by incubating a biological fluid specimen in the presence of mixture of an S-acyl compound and a chromogenic sulfhydryl reagent under conditions conducive to the lipase catalyzed release of sulfhydryl groups from the S-acyl compound and formation of color on the reaction of released sulfhydryl groups with the chromogenic sulfhydryl reagent, and measuring the color produced, the improvement which comprises:
   (a) terminating the incubation by adding to the mixture sufficient of a non-ionic sufactant to disrupt micelles and clairfy the mixture;
   (b) measuring color directly in the resulting mixture;
   (c) carrying out said steps of incubating, terminating the incubation and measuring color with a chemical color standard comprising a predetermined amount of a diagnostically-acceptable S-(aminoloweralkyl)isothiuronium salt; and
   (d) comparing the color obtained with said salt and the color obtained with said biological fluid specimen.
5. Method of claim 4 wherein the improvement further comprises adding sufficient acid to the mixture where the incubation is terminated to lower the pH sufficiently to inactivate lipase and stabilize the color.

* * * * *